（12） United States Patent
Oh et al.

(10) Patent No.: US 8,738,315 B2
(45) Date of Patent: May 27, 2014

(54) DIGITAL DAMPING CONTROL OF NANOMECHANICAL TEST INSTRUMENTS

(75) Inventors: Yunje Oh, Medina, MN (US); Matthew R. Wilson, Madison, WI (US); Ryan Charles Major, Crystal, MN (US); Syed Amanula Syed Asif, Bloomington, MN (US); Oden L. Warren, New Brighton, MN (US)

(73) Assignee: Hysitron Incorporated, Minneapolis, MN (US)

( * ) Notice: Subject to any disclaimer, the term of this patent is extended or adjusted under 35 U.S.C. 154(b) by 1359 days.

(21) Appl. No.: 12/498,238

(22) Filed: Jul. 6, 2009

(65) Prior Publication Data
US 2010/0036636 A1 Feb. 11, 2010

Related U.S. Application Data

(60) Provisional application No. 61/077,988, filed on Jul. 3, 2008.

(51) Int. Cl.
*G06F 19/00* (2011.01)
(52) U.S. Cl.
USPC .......................................... 702/113; 73/780
(58) Field of Classification Search
USPC ........................................ 702/113; 73/780
See application file for complete search history.

(56) References Cited

U.S. PATENT DOCUMENTS

2007/0180924 A1* 8/2007 Warren et al. .................. 73/780

OTHER PUBLICATIONS

Ganor et al., High sensitivity nanoscale mapping of elastic moduli, American Institute of Physics, 2006, 3 pgs.
Syed Asif et al., Nanoindentation and contact stiffness measurement using force modulation with a capacitive load-displacement transducer, Review of Scientific Instruments, vol. 70, No. 5, May 1999, pp. 2408-2413.
Anczykowski et al., Analysis of the interaction mechanisms in dynamic mode SFM by means of experimental data and computer simulation, Materials Science & Processing, 1998, 5 pgs.
Jalili et al., A review of atomic force microscopy imaging systems: application to molecular metrology and biological sciences, Mechatronics, Elsevier, #14, 2004, pp. 907-945.

* cited by examiner

*Primary Examiner* — John Breene
*Assistant Examiner* — Hien Vo
(74) *Attorney, Agent, or Firm* — Dicke, Billig & Czaja PLLC

(57) ABSTRACT

A method of damping control for a nanomechanical test system, the method including providing an input signal, providing an output signal representative of movement of a displaceable probe along an axis in response to the input signal, performing a frequency-dependent phase shift of the output signal to provide a phase-shifted signal, adjusting the phase-shifted signal by a gain value to provide a feedback signal, and adjusting the input signal by incorporating the feedback signal with the input signal.

24 Claims, 7 Drawing Sheets

DIGITAL DAMPING CONTROL OF NANOMECHANICAL TEST INSTRUMENTS

CROSS-REFERENCE TO RELATED APPLICATIONS

This Utility Patent Application claims benefit of U.S. Provisional Application 61/077,988, filed Jul. 3, 2008, and which is incorporated herein by reference.

BACKGROUND

Nanomechanical tests, such as nanoindentation (see References 1, 2 and 3), nano-tensile testing (see Reference 4), and nano-scratch test (see Reference 5), for example, are modern characterization methods to quantitatively evaluate mechanical properties of a sample at nanoscale. To obtain accurate mechanical properties, the force and displacement of a testing probe must be precisely controlled and monitored. However, in some environments, such as vacuum environments, the testing probe can experience serious motion control problems due to extremely low air damping in vacuum environments. For example, in a high vacuum/low damping environment, there is an increase in the mechanical amplification at the resonance frequency and an increase in the overall system settling time. Additionally, the low damping environment present in a high vacuum affects mechanical behavior by allowing large disturbing vibrations that create an unstable divergence in the closed loop control during nanomechanical testing. To solve the problems inherent in performing nanomechanical testing or scanning probe microscopy in a high vacuum, increasing the system damping is highly desired.

Damping controls have been attempted with many different methods and instruments (see Reference 6-16). One method is referred to as Q-control (see Reference 12). Q-control is designed for nanoscale measurement instruments, especially for the intermittent contact mode utilized in scanning probe microscopy (see Reference 11). This Q-control is realized with an analog circuit and, although it can be used to modify the system damping, it has limitations when applied to a broad range of bandwidth. Utilizing the Q-control, the bandwidth of the phase shifting circuit should be adjusted to manipulate the mechanical quality factor (Q) of the system near a certain resonance frequency and, for different frequency regions; a different circuit bandwidth is required. In addition, this analog damping controller is implemented into testing instruments as an add-on device, resulting in a more complicated hardware configuration.

Another damping control algorithm implemented with atomic force microscopes employs a trigonometric lookup table (see References 13, 14, and 15). This damping control algorithm is also designed for intermittent contact topography scanning and dynamic force spectroscopy with an oscillating probe operating at a specific frequency. This digital damping control, however, only works when oscillating the probe at a certain frequency and cannot be implemented in order to increase the system damping in non-oscillating motion control. With such a control system, the typical maximum Q modification is about 5 times the unmodified Q value (see Reference 13).

However, such a performance level falls short for effectively damping down the vibrating device in nanomechanical testers used in high vacuum. Mechanical testers used in high vacuum usually have a high Q value (e.g. 6,000), and it is recommended to decrease the Q value by about 1,000 times to be reasonably controllable.

One known feedback influenced Q-control system (see Reference 10) changes the damping characteristics of the system. This known Q-control system is based on modifying the test system in a closed loop control scheme and the damping is modified through the use of PID (proportional-integral-derivative) controller gains. While damping modification with PID control can increase the force sensitivity of the oscillating force probe by enhancing the system Q value, adjusting the Q value using the PID gains results in a dynamic system having a small phase margin for dynamic stability.

In short, reducing the system quality factor in nanomechanical testers in high vacuum is highly desirable because it can shorten the settling time and improve the stability in a closed loop control mode. Although reducing the system quality factor is important for high measurement accuracy, to date, no active damping controller is known to have been developed for nanomechanical testing in high vacuum.

REFERENCES

1. A. C. Fisher-Cripps, *Nanoindentation* (Springer, New York, 2004).
2. "Review of instrumented indentation", M. R. VanLandingham, *J. Res. Natl. Inst. Stand. Technol.* 108, 249 (2003).
3. "An improved technique for determining hardness and elastic modulus using load and displacement sensing indentation measurements", W. C. Oliver and G. M. Pharr, *J. Mater. Res.* 7, 1564 (1992).
4. Application note from Hysitron, Inc. titled "Nanotensile characteristics of metal wires", Xiao, Q., Schirer, J., Tsuchiya, F., and Yang, D., 2007.
5. Gerberich, W. W., N. I. Tymiak, and D. E. Kramer, "Fundamental Aspects of Friction and Wear Contacts in (100) Surfaces", Mat. Res. Soc. Proc. Vol. 649, 2001.
6. "Active control precision damping table", Choshitani, H., Osaka, T., Itojima, F., and Yasuda, M., U.S. Pat. No. 5,060,519, 1991.
7. "Damped control of a micromechanical device", 2006, Chu, H. C.-H., Gonzalez, A., and Oudal, T. D., U.S. Pat. No. 6,985,278 B2.
8. "Damped control of a micromechanical device", 2005, Hewlett, G. J. and McDonald, W. C., U.S. Pat. No. 6,891,657 B2.
9. "Hearing aid having digital damping", 2002, Killion, M. C., Papalias, C. W., Becker, A. J., and Mapes-Riordan, D., U.S. Pat. No. 6,466,678 B1.
10. "Feedback influenced increased-quality-factor scanning probe microscope", 2006, Warren, O. L., Norton, P. R., and Graham, J. F., U.S. Pat. No. 7,425,698.
11. "Analysis of the interaction mechanism in dynamic mode SFM by means of experimental data and computer simulation", 1998, Anczykowski, B., Cleveland, J. P., Krüger, D., Elings, V., and Fushs, H., Applied Physics A, Vol. 66, S885-S889.
12. Q-Control brochure, nanoAnalytics GmbH, 2008.
13. MFP-3D AFM brochure, Asylum Research, 2008.
14. "Digital control of quality factor in resonant systems including cantilever based instruments", Bocek, D. and Cleveland, J., U.S. Pat. No. 7,165,445 B2, 2007.
15. "Digital Q control for enhanced measurement capability in cantilever-based instruments", Bocek, D. and Cleveland, J., US Patent US2007/0157711 A1, 2007.
16. PicoIndenter brochure, Hysitron Inc., 2008.

SUMMARY

One embodiment provides a method of damping control for a nanomechanical test system, the method including providing an input signal, providing an output signal representative of movement of a displaceable probe along an axis in response to the input signal, performing a frequency-dependent phase shift of the output signal to provide a phase-shifted signal, adjusting the phase-shifted signal by a gain value to provide a feedback signal, and adjusting the input signal by incorporating the feedback signal to the input signal.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
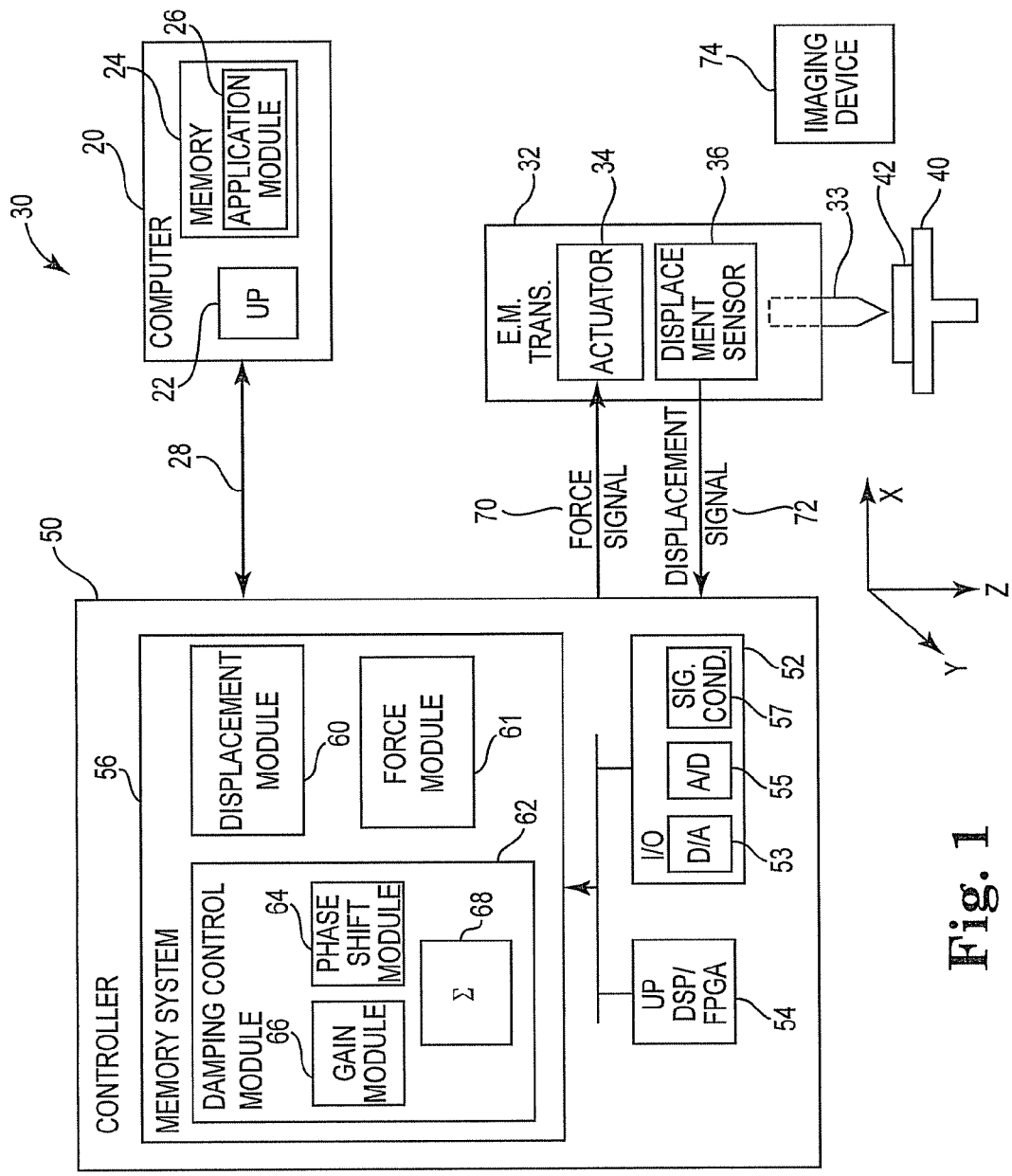
FIG. 1 is a block diagram generally illustrating a nanomechanical testing system employing digital damping control according to one embodiment.

FIG. 1 is a block diagram generally illustrating an example of a nanomechanical test system 30 employing active damping control to control the system quality factor, Q, and modify system damping (e.g. increase or decrease system damping), according to embodiments of the present disclosure. Nanomechanical test system 30 includes an electromechanical transducer 32 having a displaceable probe 33, an actuator 34, and a displacement sensor 36, a holder or platform 40 for holding a test material or sample 42, a controller 50, and a computer 20.

According to one embodiment, controller 50 includes an input/output module 52, a processor 54, such as microprocessor or digital signal processor (DSP) and/or field programmable gate array (FPGA), for example, and a memory system 56. According to one embodiment, memory system 56 includes a displacement module 60, a force module 61, and a damping control module 62, with damping control module 62 further including a phase shift module 64, a gain module 66, and an adjuster module 68. According to one embodiment, input/output module 52 further includes a D/A converter 53, an A/D converter 55, and a signal conditioner 57. According to one embodiment, computer 20 includes a processor 22 and a memory system 24 storing an application module 26. Computer 20 may access and communicate with controller 50 via an interface 28 (e.g. a USB interface). Although illustrated in FIG. 1 as comprising separate entities, it is noted that, in other embodiments, computer 20 and controller 50 may be combined as part of a single processing or control system.

According to one embodiment, application module 26 and displacement module 60, force module 61 and damping control module 62 each comprise instructions respectively stored in memories 24 and 56 and which are accessible and executable by a processor 54. Memories 24 and 56 may comprise any number of types of volatile or non-volatile storage devices such as RAM, hard disk drives, CD-ROM drives, and DVD drives, for example. In other embodiments, displacement module 60, force module 61, and damping control module 62 may comprise any combination of hardware and software components configured to perform functions described herein. The software component of displacement module 60, force module 61, and damping control module 62 may each be stored on a medium separate from processing system 54 prior to being stored in memory system 56. Examples of such a medium include a hard disk drive, a compact disc (e.g. a CD-ROM, CD-R, or CD-RW), and a digital video disc (e.g. a DVD, DVD-R, and DVD-RW), for example.

According to one embodiment, controller 50, via application module 26 on computer 20, is configured to control and monitor the movement of displaceable probe 33 relative to sample 42, and to provide to computer 20 via interface 28 data representative of a displacement of displaceable probe 33. According to one embodiment, controller 50 is configured to determine and adjust a force applied to sample 42 by displaceable probe 33.

In operation, the user can program the controller 50 using computer 20 with application module 26. According to one embodiment, controller 50, via force module 61 provides an input or force signal 70 representative of a desired force to actuator 34 of electromechanical transducer 32. In response, actuator 34 drives displaceable probe 33 toward sample 42 (i.e. along the z-axis in FIG. 1) such that displaceable probe 33 contacts and applies the desired force to sample 42. D/A converter 53 converts the input or force signal provided by force module 61 from digital to analog form which, in turn, is amplified by signal conditioner 57 to generate force signal 70 as provided to actuator 34.

Displacement sensor 36 comprises a transducer (e.g. a capacitive transducer) which detects movement of displaceable probe 33 at least along the z-axis, and provides a displacement signal 72 to controller 50 representative of such movement of displaceable probe 33. In other embodiments, in addition to movement along the z-axis, displacement sensor 36 detects and provides indication of other types of movement of displaceable probe 33, such as displacement along the x- and/or y-axes or rotational movement about the x- and/or y-axes, for example. Signal conditioner 57 extracts the desired range of signals from the displacement signal 72. A/D converter 55 converts displacement signal 72 from an analog form, as received from displacement sensor 36, to a digital form for processing by displacement module 60 which, according to one embodiment, provides indication of the movement of displaceable probe 33 to force module 61 (e.g. for force calculations) and computer 20.

According to one embodiment, controller 50, via displacement module 60, force module 61, and damping control module 62, provides a Q-controlled or Q-adjusted force signal 70 to actuator 34 to actively control the system damping of nanomechanical test system 30 based on movement of displaceable probe 33 provided by displacement sensor 36 via displacement signal 72. The active damping control of nanomechanical test system 30 by damping control module 62 is described in greater detail below by FIG. 2. In general, the so-called Q-factor or mechanical quality factor, Q, defines the damping of a moveable part or component of a system, such as displaceable probe 33. Conventionally, the lower the value of a system's Q factor, the greater the system damping, and vice-versa.

According to one embodiment, controller 50 is further configured to control movement or displacement of displaceable probe 33 in the x- and y-directions relative to sample 42, such as by moving electromechanical transducer 32 relative to sample 42 or by moving sample 42 relative to electromechanical transducer 32 (e.g. by moving sample holder 40). According to one embodiment, nanomechanical test system 30 further includes an imaging device 74 comprising an instrument/device such as an optical microscope or a scanning probe microscope (SPM) (e.g., an atomic force microscope (AFM)) configured to provide images of sample 42.

Examples of test systems suitable to be configured for use with the damping control scheme of the present disclosure are described by U.S. Pat. Nos. 5,553,486 and 5,869,751, both of which are assigned to the same assignee as the present disclosure and incorporated herein by reference. Another test system suitable to be configured for use with the digital damping scheme of the present disclosure is an electron microscopy (EM) (transmission electron microscopy and/or scanning electron microscopy) in-situ nanomechanical tester commercially available under the tradename PicoIndenter from Hysitron, Incorporated, of Minneapolis, Minn., USA.

Figure 2:
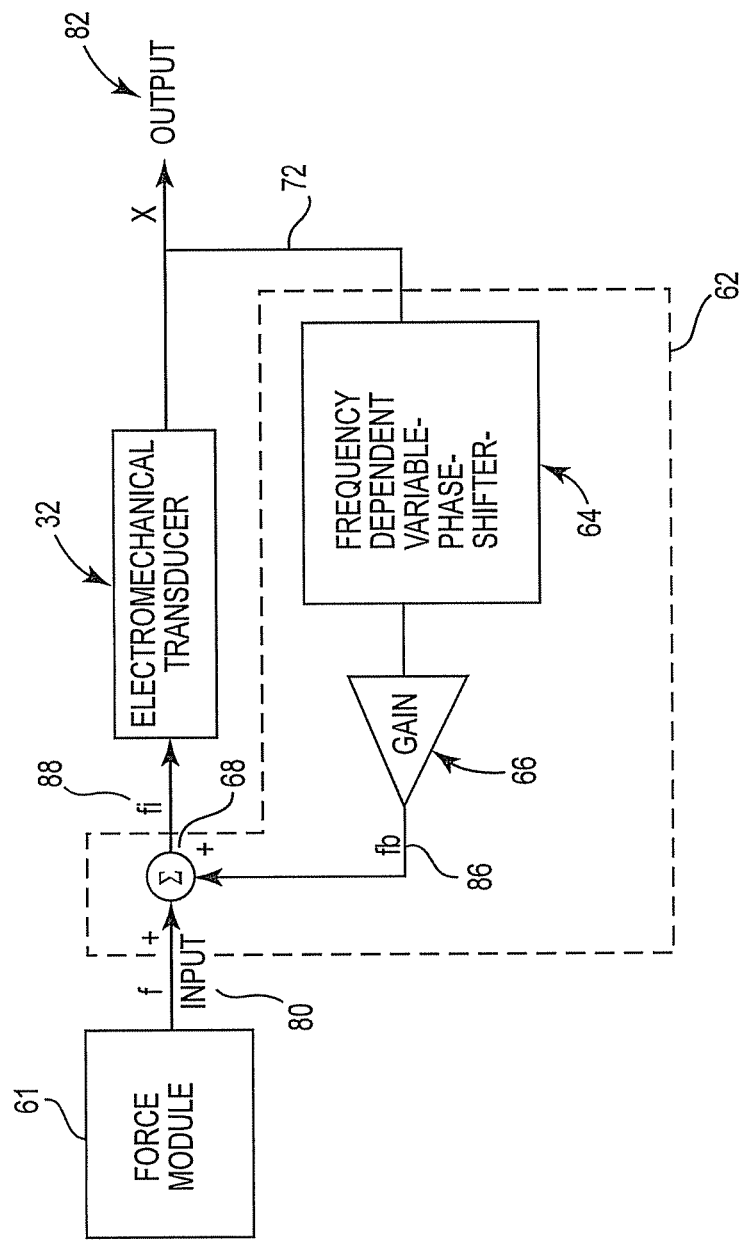
FIG. 2 is a block and schematic diagram illustrating a digital damping scheme according to one embodiment.

FIG. 2 is a block and schematic diagram which generally illustrates and models a digital damping control scheme, according to embodiments of the present disclosure, for controlling the system damping of nanomechanical test system 30. In the absence of system damping provided by damping control module 62, force module 61 provides an unmodified force signal, f, which is representative of a desired force, directly to actuator 34 of electromechanical transducer 32 resulting in actuator 34 moving displaceable probe 33 along the z-axis by a distance that results in displaceable probe 33 applying the desired force to test sample 42.

In FIG. 2, the unmodified force signal, f, provided by force module 61, sometimes referred to as the excitation input signal, is illustrated as an input f at 80, with the resulting movement of displaceable probe 33 along the z-axis from the resulting response of actuator 34 being illustrated as an output x, at 82.

When the dynamic motion of the displaceable probe 33 has a second order linear characteristic, as is the case here, the dynamic motion of displaceable probe 33 along the z-axis resulting from application of unmodified force f can be expressed by a system equation as represented by Equation I as follows:

$$f = m\ddot{x} + c\dot{x} + kx;$$ EQ. I where x is the testing probe motion, in this case along the z-axis, and m, c, k are the mass, damping coefficient, and stiffness of displaceable probe 33, respectively.

The movement, x, of displaceable probe 33 at a frequency ω at output 82 can be expressed by Equation II as follows:

$$x = X \cos \omega t$$ EQ. II where X is the vibration amplitude, ω is the angular frequency, and t is the time.

According to one embodiment, a signal representative of the movement of displaceable probe 33 at the vibration frequency ω, such as displacement signal 72 provided by displacement sensor 36, is 90-degree shifted in the positive direction by frequency-dependent variable-phase-shift module 64 and adjusted by a gain, G, of the gain module 66 to provide a feedback signal, fb, as indicated at 86, which can be expressed by Equation III as follows:

$$fb = GX \sin \omega t$$ EQ. III

Feedback signal fb 86 is then incorporated with the excitation input signal f80 by adjuster module 68 to form a modified system equation or excitation input, $f_1$, as indicated at 88. According to one embodiment, adjuster module 68 incorporates feedback signal fb 86 with input signal f80 by adding feedback signal fb 86 with input signal f80 to form modified input $f_1$, which can be expressed by Equation IV as follows:

$$f_1 = m\ddot{x} + \left(c + \frac{G}{\omega}\right)\dot{x} + kx.$$ EQ. IV

Comparing the unmodified system or excitation input equation of Equation I, without the damping control of damping control module 62, with the modified system or excitation input equation of Equation IV, with the damping control of damping control module 62, the Q-controlled system's adjusted damping coefficient CA is represented by Equation V as follows:

$$c_A = \left(c + \frac{G}{\omega}\right).$$ EQ. V

Rewriting the adjusted damping coefficient CA in terms of the system's mechanical quality factor provides the following relation as described by Equation VI below:

$$Q_{adj} = \left[\frac{1}{Q} + \frac{G}{k}\frac{\omega_n}{\omega}\right]^{-1},$$ EQ. VI where $Q_{adj}$ is the adjusted system quality factor, Q is the system quality factor without system modification, and $\omega_n$ is the natural frequency.

Based on Equation VI above, when the input excitation is close to the natural frequency ($\omega \approx \omega_n$), the adjusted system quality factor is simplified as illustrated by Equation VII below:

$$Q_{adj} = \left[\frac{1}{Q} + \frac{G}{k}\right]^{-1}.$$ EQ. VII

From Equation VII above, it can be seen the value of adjusted system quality factor $Q_{adj}$ at $\omega_n$ can be tuned simply by modifying the gain, G, of gain module 66.

According to one embodiment, the above described damping control scheme of damping control module 62 is implemented into a PicoIndenter (see Reference 14), a nanomechanical testing instrument designed for use in high vacuum, using digital signal processing. For such a damping control implementation, the phase shifting of phase shift module 64 is performed using the following transfer function as expressed by Equation VIII below:

$$\frac{V_{out}}{V_{in}}(j\omega) = \frac{\omega_n - j\omega}{\omega_n + j\omega};$$ EQ. VIII where $V_{in}$ represents the input to phase shifter 64 (e.g. displacement signal 72), $V_{out}$ represents the phase shifted output of phase shifter 64 (e.g. to gain module 66), and $j=\sqrt{-1}$. This transfer function is expressed in frequency domain to describe the phase shifting concept.

Figure 3:
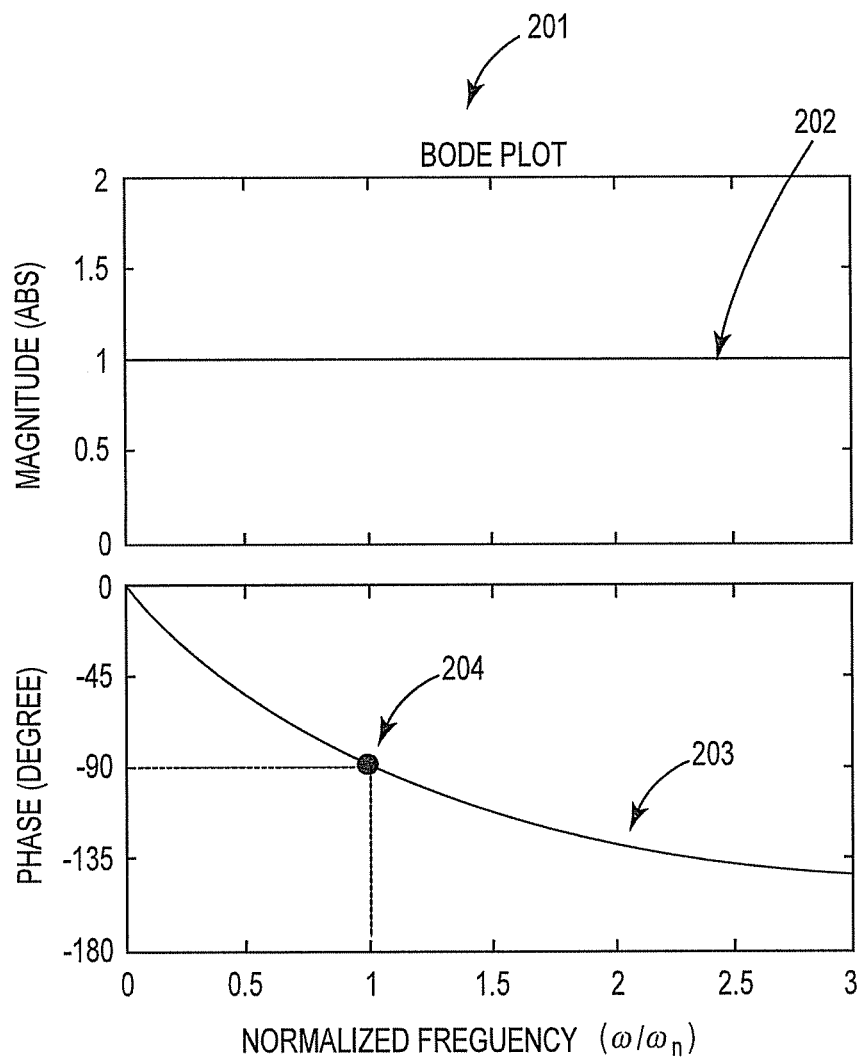
FIG. 3 is a Bode plot of a transfer function employed by a digital damping control according to one embodiment.

FIG. 3 is a Bode plot 201 of the transfer function represented by Equation VIII. It is noted that actual digital implementation was done with a transfer function in a discrete domain. A magnitude 202 of the transfer function is always 1 regardless of the natural frequency $\omega_n$ and the vibration frequency $\omega$. This transfer function shifts the phase 203 by 90° at $\omega=\omega_n$, as indicated at 204. According to one embodiment, this frequency is chosen to coincide with the natural frequency of the dynamics of displaceable probe 33 of nanomechanical test system 30 and shifts the phase by 90° at the natural frequency which makes the damping control more efficient.

According to one embodiment, for digital implementation, the Laplace transform of the phase shifting transfer function $$\frac{V_{out}}{V_{in}}(s) = \frac{\omega_n - s}{\omega_n + s}$$

is z-transformed by replacing s with $$\frac{2(z-1)}{T(z+1)},$$

where T is the sampling interval. As a result, the discrete phase shifting transfer function may then be expressed as Equation IX below:

$$\frac{V_{out}}{V_{in}}(z) = \frac{\omega_n - s}{\omega_n + s}\bigg|_{s=\frac{2(z-1)}{T(z-1)}}.$$ EQ. IX As described above, the digital damping control scheme of damping control module 62 can either increase or decrease the system quality factor Q by manipulating (e.g., increasing or decreasing) the damping controller gain.

Figure 4:
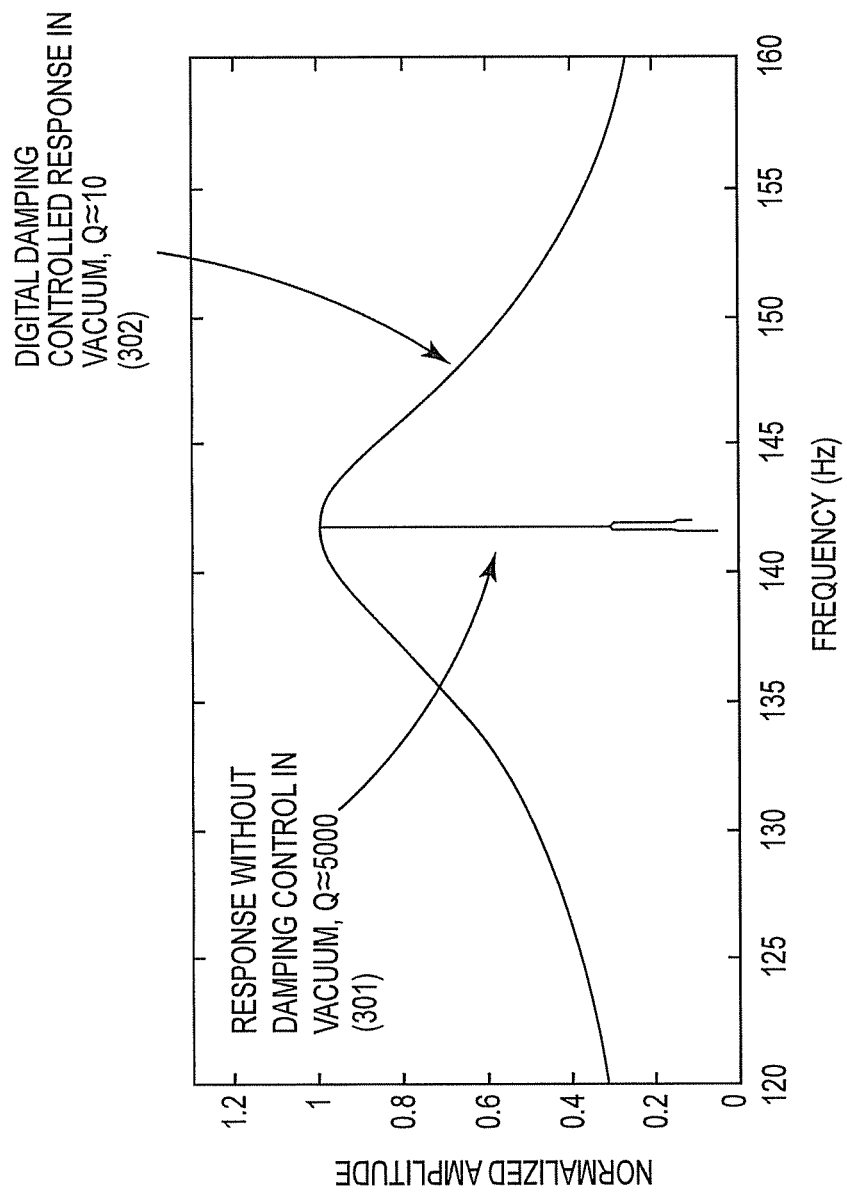
FIG. 4 is a graph illustrating a frequency response of a Picoindenter with and without digital damping control according to one embodiment.

According to one implementation, the frequency responses of the PicoIndenter (see Reference 16) were measured to prove the functionality of the digital damping control techniques according to the embodiments described herein. According to one embodiment, as illustrated by FIG. 4, the frequency response of the system without damping control was measured to have the Q value of 5000, as indicated at 301. After "turning on" the digital damping control scheme of damping control module 62, the frequency response showed a wider bandwidth resonance peak and a Q value of 10, as indicated at 302.

Figure 5:
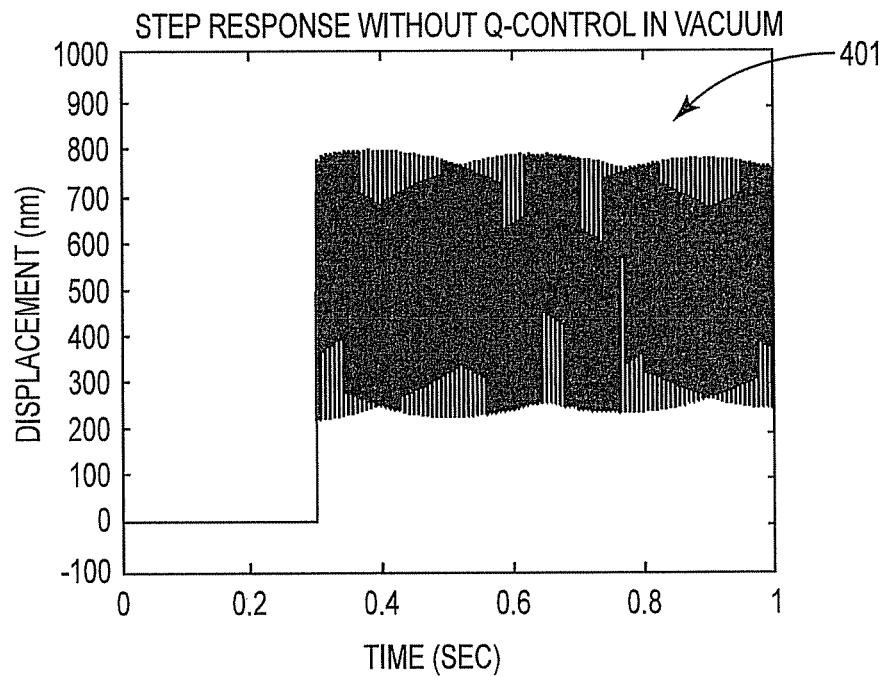
FIG. 5 is a diagram illustrating a step response with and without digital damping control according to one embodiment.
Figure 5:
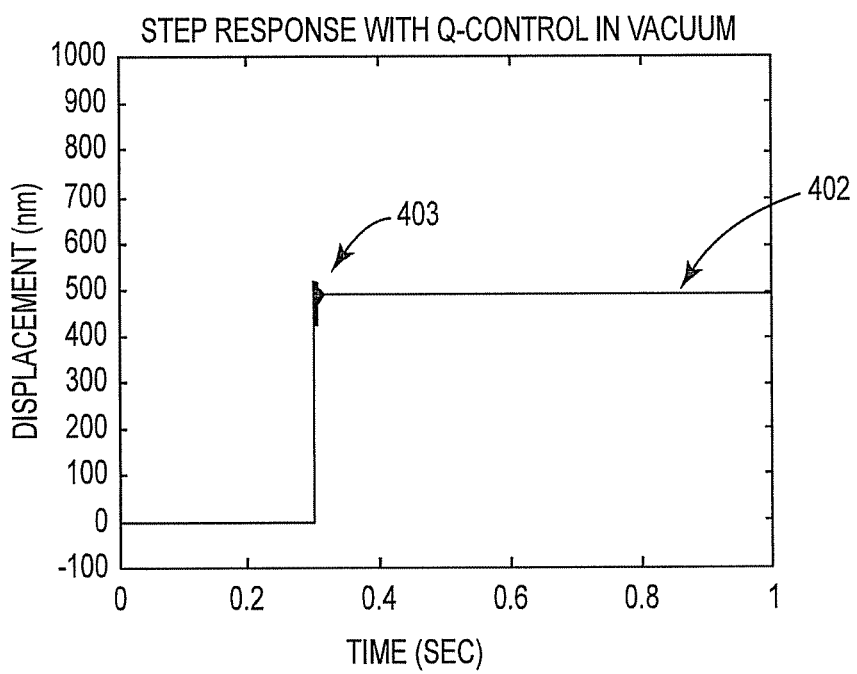

Another measurement was performed illustrating how the Q value changes a step response of the system. As illustrated by FIG. 5, a step response without the damping control of the present disclosure in vacuum resulted in a low damping characteristic with a large overshoot and long settling time, as indicated at 401. In contrast, after the digital damping control of damping control module 62 was "turned on", the step response showed increased damping characteristic with a smaller overshoot 403 and a faster settling time, as indicated at 402.

From the above discussion, it is noted that nanomechanical test system 30 can be operated both with and without the damping control mode by turning on and off the damping control module 62.

Figure 6:
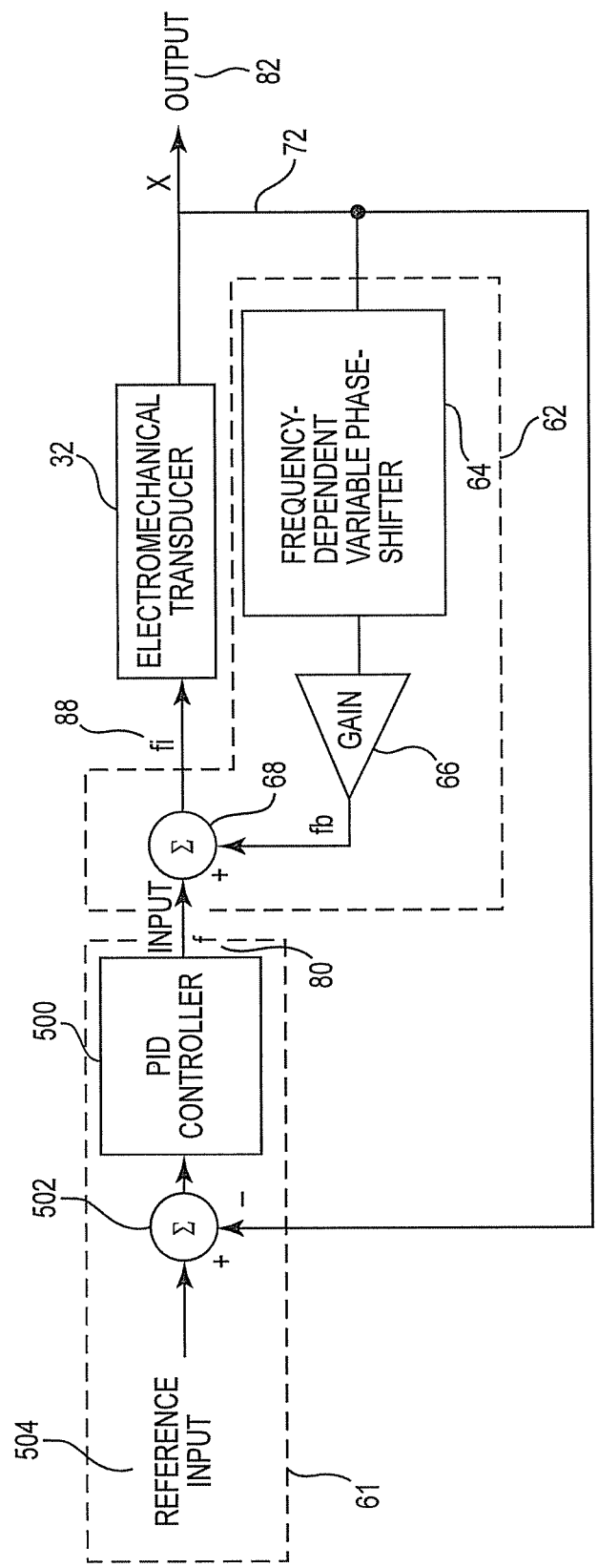
FIG. 6 is a block and schematic diagram generally illustrating a nanomechanical testing system employing digital damping control according to one embodiment.

FIG. 6 is a schematic and block diagram further illustrating nanomechanical test system 30 of FIG. 1 when the digital damping control of damping control module 62 is combined with a PID controller 500 (proportional-integral-derivative controller). According to one embodiment, PID controller 500 and an adder 502 are implemented as part of force module 61 and implemented as instructions stored in memory system 56 which are accessible and executable by processor 54. According to one embodiment, adder 502 determines an error between the actual displacement, x, of displaceable probe 33 as provided by displacement signal 72 of displacement sensor 36 and a reference input 504 which is representative of a desired displacement of displaceable probe 33 in response to input signal 80. According to one embodiment, reference input 504 comprises predetermined displacement profile(s) of the desired or expected displacement of displaceable probe 33 which are stored in memory system 56. The error provided by adder 502 is acted upon by control feedback provided by PID controller 500 to adjust input signal 80 provided by force module 61. It is noted, as described earlier, that PID type controllers are employed by some conventional nanomechanical test systems, but not in combination with the digital damping techniques according to the present disclosure.

Figure 7:
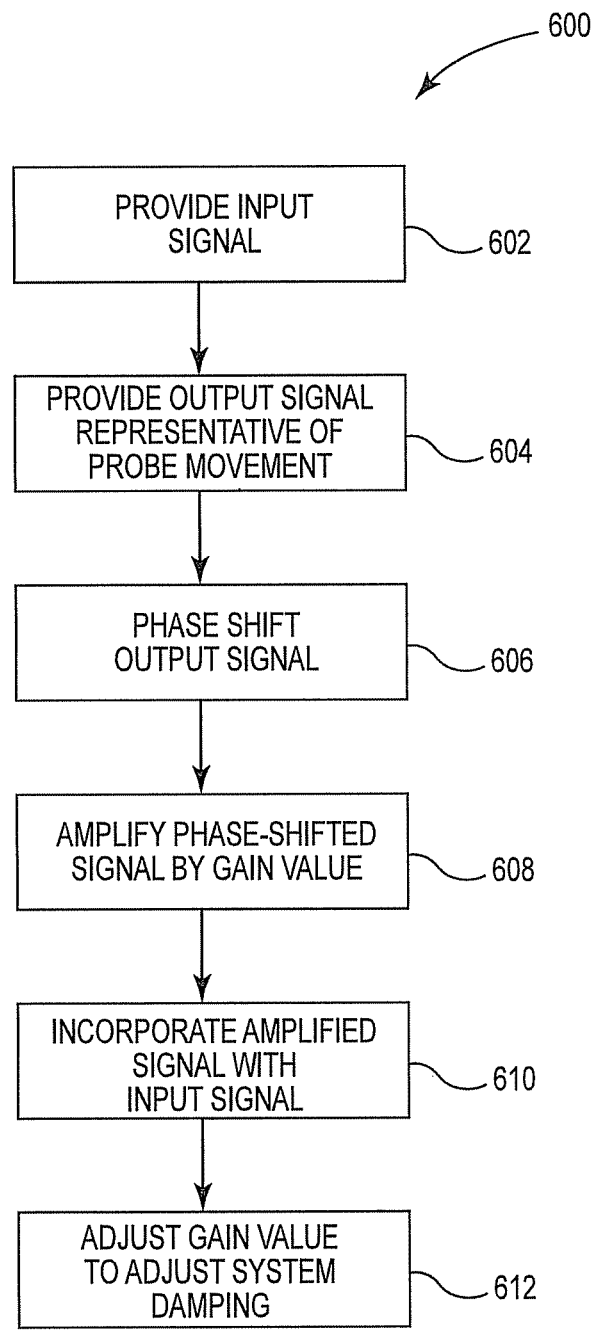
FIG. 7 is a flow diagram generally illustrating a damping process for a nanomechanical test system according to one embodiment.

FIG. 7 is a flow diagram generally illustrating one embodiment of a process 600 for operating a nanomechanical test system employing digital damping techniques, according to embodiments described herein, to control system damping. Process 600 begins at 602 with the providing of an input signal, such as input signal 80 as provided by force module 61. At 604, an output signal representative of movement of a displaceable probe is provided, such as displacement signal 72 as provided by displacement sensor 36.

At 606, the output signal is phase shifted, such as by frequency-dependent variable phase shifter 64. At 608, the resulting phase-shifted output signal is modified by a gain value to form a feedback signal, such as by gain module 66. Although described herein primarily as amplifying the phase-shifted output signal, it is noted that the gain value may also have a value less than or equal to one such that gain module 66 is not necessarily functioning as an amplifier, but to adjust or modify a magnitude of the phase-shifted output signal. At 610, the feedback signal is incorporated into the input signal. At 612, according to one embodiment, a mechanical quality factor, Q, of the nanomechanical test system is adjusted to achieve a desired quality factor by selecting an appropriate gain value.

Although described primarily herein in terms of damping motion in a single direction, in particular, to control the damping of displaceable probe 33 along the z-axis, the digital damping techniques described herein can be applied to movements of nanomechanical test system 30 in other directions as well. For example, in addition to controlling damping of displaceable probe 33, the damping control techniques described herein may be employed by controller 50 to damp vibrations of electromechanical transducer 32 as it is moved along the x- and or y-axes.

Additionally, although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that digital damping techniques according to the present disclosure be limited only by the claims and the equivalents thereof.

What is claimed is:

1. A method of operating a nanomechanical test system having a displaceable probe, the method comprising:
   providing, using a processor of a processing system, an input signal to the displaceable probe;
   providing, from a displacement sensor, an output signal representative of movement of the displaceable probe along an axis in response to the input signal;
   performing, using the processor, a frequency-dependent phase shift of the output signal to provide a phase-shifted signal;
   adjusting, using the processor, the phase-shifted signal by a gain value to provide a feedback signal;
   adjusting, using the processor, the input signal by incorporating the feedback signal with the input signal to modify a mechanical quality factor of the nanomechanical so as to actively control mechanical damping of the nanomechanical test system.

2. The method of claim 1, wherein incorporating comprises adding the feedback signal to the input signal.

3. The method of claim 1, including adjusting the gain value to achieve a desired mechanical damping of the nanomechanical test system.

4. The method of claim 1, including adjusting a magnitude of the gain value to achieve a desired mechanical quality factor.

5. The method of claim 1, herein performing the frequency-dependent phase shift includes employing a transfer function which shifts the phase from 0 to 180 degrees from a low frequency to high frequency and has a unity magnitude for the entire frequency range.

6. The method of claim 5, including performing a 90 degree phase shift at a resonance frequency of the moveable probe.

7. A nanomechanical test system comprising:
   a displaceable probe;
   an actuator configured to move the displaceable probe along an axis in response to an input signal;
   a displacement sensor configured to provide an output signal representative of movement of the displaceable probe along the axis;
   a phase shift module configured to perform a frequency-dependent phase shift of the output signal to provide a phase-shifted signal;
   a gain module adjusting the phase-shifted signal by a selectable gain value to provide a feedback signal;
   an adjuster module configured to adjust the input signal by incorporating the feedback signal with the input signal, wherein a system damping of the nanomechanical test system is adjustable based on the selectable gain value.

8. The nanomechanical test system of claim 7, wherein incorporating comprises adding the feedback signal to the input signal.

9. The nanomechanical test system of claim 7 wherein a mechanical quality factor of the nanomechanical test system is tunable by modifying the gain value.

10. The nanomechanical test system of claim 7, wherein a mechanical quality factor of the nanomechanical test system is adjustable by an amount of phase shift provided by the phase shifter.

11. The nanomechanical test system of claim 7, wherein the nanomechanical test system is operated in non Q control mode and when the gain value is set to zero.

12. The nanomechanical test system of claim 7, wherein the phase shifter has a transfer function which shifts the phase from 0 to 180 degrees from a low frequency to high frequency and has a unity magnitude for the entire frequency range.

13. The nanomechanical test system of claim 12, wherein a 90 degree phase shift is performed at a resonance frequency of the moveable probe.

14. A nanomechanical test system comprising:
   an actuator configured to move a displaceable probe along an axis in response to an input signal;
   a displacement sensor configured to provide an output signal representative of movement of the displaceable probe along the axis by the actuator;
   a memory system including:
     a force module;
     a phase shift module;
     a gain module; and
     an adjustment module; and
   a processor configured to:
     execute the force module to provide the input signal;
     execute the phase shift module to perform a frequency-dependent phase shift of the output signal to provide a phase-shifted signal;
     execute the gain module to adjust the phase-shifted signal by a selectable gain to provide a feedback signal; and
     execute the adjustment module to adjust the input signal by incorporating the feedback signal with the input signal.

15. The nanomechanical test system of claim 14, wherein incorporating the feedback signal with the input signal comprises adding the feedback signal to the input signal.

16. The nanomechanical test system of claim 14, wherein the processor is configured to execute the gain module to adjust the gain to adjust a system damping of the nanomechanical test system based on user input to the gain module via an input/output.

17. The nanomechanical test system of claim 14, wherein the processor is configured to execute the gain module to adjust the gain to adjust a mechanical quality factor of the nanomechanical test system based on user input to the gain module via an input/output.

18. The nanomechanical test system of claim 14, wherein the frequency-dependent phase shift performed via execution of the phase shift module by the processor has a transfer function which shifts the phase from 0 to 180 degrees from a low frequency to a high frequency and has a unity magnitude for the entire frequency range.

19. The nanomechanical test system of claim 18, wherein a 90 degree phase shift is performed at a resonance frequency of the displaceable probe.

20. The nanomechanical system of claim 14, wherein the displacement module includes a PID (proportional-integral-derivative) controller, an adder, and a reference input representative of a desired movement of the displaceable electrode, wherein the processor executes the adder to determine a displacement error between the reference input and the output signal, and executes the PID controller to provide the input signal based on the displacement error.

21. The nanomechanical test system of claim 14, wherein the nanomechanical test system is operated in non Q control mode when the gain value is set to zero.

22. A non-transitory computer-readable medium including instructions executable by a computer for performing a process of active mechanical damping control for a nanomechanical test system having a displaceable probe, the process comprising:
- providing an input signal for actuation of the displaceable electrode
- receiving a displacement signal representative of movement of the displaceable probe along an axis in response to the input signal;
- performing a frequency-dependent phase shift of the displacement signal to provide a phase-shifted signal;
- adjusting the phase-shifted signal by a gain value to provide a feedback signal;
- adjusting the input signal by incorporating the feedback signal with the input signal to modify the mechanical damping of the nanomechanical test system.

23. The non-transitory computer readable medium of claim 22, wherein incorporating comprises adding the feedback signal to the input signal.

24. The non-transitory computer readable medium of claim 22, further including instructions for adjusting the gain value to adjust damping of the displaceable probe based on user input.

* * * * *